United States Patent [19]

Richter et al.

[11] Patent Number: 4,521,221
[45] Date of Patent: Jun. 4, 1985

[54] METHOD OF PRODUCING A METHANE-RICH GAS MIXTURE FROM MINE GAS

[75] Inventors: Ekkehard Richter, Essen; Werner Körbächer, Mülheim; Karl Knoblauch, Essen; Klaus Giessler, Gelsenkirchen, all of Fed. Rep. of Germany

[73] Assignee: Bergwerksverband GmbH, Essen, Fed. Rep. of Germany

[21] Appl. No.: 582,433

[22] Filed: Feb. 22, 1984

[30] Foreign Application Priority Data

Feb. 24, 1983 [DE] Fed. Rep. of Germany ....... 3306371

[51] Int. Cl.³ .............................................. C10K 3/00
[52] U.S. Cl. ................................. 48/196 R; 48/197 R; 55/25; 55/62; 166/267
[58] Field of Search ............. 48/196 R, 197 R; 55/25, 55/26, 62, 68, 75; 585/825; 166/266, 267

[56] References Cited

U.S. PATENT DOCUMENTS 3,164,454  1/1965  Wilson ..................................... 55/68
4,305,734 12/1981  McGill ..................................... 55/25
4,475,929 10/1984  Fuderer .................................... 55/25

Primary Examiner—Peter Kratz
Attorney, Agent, or Firm—Karl F. Ross; Herbert Dubno

[57] ABSTRACT

A pressure-swing adsorption system is used to enrich the methane content of mine gas obtained from bores around mine shafts or galleries from the customary 25 to 45% by volume to a product gas quality of 50% by volume. Using a carbon molecular sieve adsorbent, the adsorption is carried out at 5 to 8 bar and is followed by a uniflow expansion to an intermediate pressure and a counterflow expansion to a flushing pressure of 1.1 to 2 bar. Counterflow flushing is carried out with waste gas and the product gas is a mixture of the gases obtained by counterflow expansion and flushing.

6 Claims, 4 Drawing Figures

METHOD OF PRODUCING A METHANE-RICH GAS MIXTURE FROM MINE GAS

FIELD OF THE INVENTION

Our present invention relates to a method of producing a methane-rich gas mixture with a substantially constant methane content from low-methane mine gases. More particularly the invention relates to the production of a product gas containing about 50 volume percent methane from low-methane naturally occurring gases utilizing pressure-swing adsorber principles.

BACKGROUND OF THE INVENTION

As will be developed in greater detail below, low-methane naturally occurring gases, frequently called mine gases, can be utilized to produce a product gas having a higher methane concentration by pressure-swing adsorber processes utilizing a plurality of adsorbers in which the adsorbent can be a carbon-based material tending selectively to adsorb methane at an elevated pressure and to desorb methane upon pressure reduction.

In such processes, the naturally occurring low-methane gas, which can be referred to as a mine gas or fire damp, is passed through an adsorber in which the adsorbent selectively adsorbs methane, the adsorbed methane is then released by dropping the pressure and the methane-rich product gas is then discharged from each adsorber.

To protect mine shafts or galleries and, in general, deep coal mining operations, especially bituminous coal mining, against the incursion of fire damp or the development of explosive conditions because of the buildup of methane in the mine atmosphere, it is known to provide bores or holes in the rock structure around the galleries, tunnels or shafts from which methane-containing gases are evacuated by suction pumps or the like. These subterranean gases, which can be described as methane-poor or low-methane gases, can be referred to for convenience as mine gases and generally contain between 25 and 45 volume percent methane together with other components such as nitrogen, oxygen and carbon dioxide.

Such gases are analogous to natural gas but, in spite of the significant methane concentration, do not contain sufficient methane for direct use as a product gas, and are also characterized by a high degree of variability in the methane concentration of the extracted gases.

The subterranean extraction of gases in this manner reduces the tendency of methane incursion into the mine shafts or galleries and thus plays a protective role.

The methane content of the recovered gases, generally above 25% by volume, is well above the upper ignition point (14 volume percent methane) although the heat value of the extracted mine gas is comparatively small, especially when, as is usually the case, the mine gas contains less than 35% by volume methane, a level below which the gas cannot practically be used as a fuel for economical reasons.

As a consequence, it is desirable to increase the methane content of the mine gas so that its heat value is substantially equal to that of the natural gas and other gases utilized for municipal heating and other purposes. To this end it is desirable to so enrich the gas in methane with the methane content will be about 50% by volume.

One obvious way to enrich the mine gas to this concentration of methane is to add liquefied methane to it. This is expensive because the production of liquefied methane is costly and hence this approach has not been utilized economically to any great extent.

In U.S. Pat. No. 4,305,734, there is described a pressure-swing adsorption method of enriching the gas with methane.

OBJECTS OF THE INVENTION

It is, therefore, the principal object of the present invention to provide an improved method of obtaining a methane-enriched product gas from mine gas derived in the aforedescribed manner and as obtained in accordance with the techniques described in the aforementioned U.S. patent whereby the disadvantages of the prior art technique are avoided and with good economy.

Another object of this invention is to provide a method of enriching mine gas in methane to substantially the quality of municipal gas at comparatively low cost, with a minimum loss of variable methane and with a substantially constant methane concentration so that fluctuations in the methane content of the starting mine gas have little or no effect.

It is also an object of this invention to provide a comparatively methane-rich gas, for heating and industrial purposes in which the methane is present in high yield.

A further object of the invention is to provide a method of producing a methane-containing gas with a substantially constant methane concentration of about 50% by volume while obviating the disadvantages of earlier methods.

SUMMARY OF THE INVENTION

These objects and others which will become apparent hereinafter are attained in a method in which the methane concentration of a mine gas containing up to 45% by volume methane is enriched to a substantially constant methane concentration of about 50 volume percent utilizing one or more adsorbers in a pressure swing adsorption system in which the methane is adsorptively retained on a adsorbent at an elevated pressure and is desorbed from the adsorbent upon a reduction of pressure. The method of the invention, however, distinguishes over the art by the combination of the following steps:

(a) adsorbing the methane from the mine gas at an adsorption pressure between substantially 5 and 8 bar by passing the mine gas through an adsorber containing a carbon molecular sieve to discharge from the adsorber a waste gas which is substantially methane free, i.e. contains at most trace amounts of methane;

(b) then expanding the adsorber in uniflow (i.e. in the same flow direction traversed during adsorption) to an expansion pressure of about 2.5 to 5 bar to produce a waste gas containing at most trace amounts of methane;

(c) thereafter expanding the adsorber in counterflow to a predetermined pressure (final or flushing pressure) between 1.1 and 2 bar to generate a portion of the product gas with a methane content of about 50% by volume in a first production step;

(d) counterflow flushing the adsorber utilizing at least one of the waste gases produced in steps (a) and (b) at a flushing pressure substantially between 1.1 and 2 bar to generate a further portion of the product gas containing about 50 volume percent methane in the second production step; and (e) building up the pressure in the adsorber utilizing at least one of the waste gases produced in steps (a) and (b) to the adsorption pressure of substantially 5 to 8 bar required for step (a), the methane content of the product gas being controlled by regulating the level of the flushing pressure so that with higher methane concentration in the mine gas, higher flushing pressures are used, thereby maintaining the methane concentration in the product gas at substantially 50% by volume. The latter parameter can mean a concentration of up to about 60% by volume.

According to a feature of the invention, the methane content of the product gas is controlled additionally or alternatively by regulating the level of the adsorption pressure in step (a) and particularly by reducing the adsorption pressure as the methane concentration of the mine gas increases.

Each of these pressure controls or combined control for the flushing pressure and the adsorption pressure can be effected by feed-back monitoring of the methane concentration of the product gas or by detecting the methane concentration of the incoming mine gas and controlling the pressure in accordance with a predetermined algorithm.

Naturally, the gas introduced in step (a) need not consist of mine gas or need not exclusively be mine gas but can be any relatively low-methane gas which it may be desirable to enrich. Preferably the enrichment is effected to a maximum methane content of the product gas of about 60% although best results are obtained when the methane content of the product gas is maintained at about 50% by volume.

It should be clear from the foregoing that the invention allows the concentration of methane in mine gas to be substantially increased utilizing the low operating cost pressure-swing adsorption process without the need for expensive highly concentrated gas mixtures or liquefied methane to be added to the product gas. This of course means that in addition to a cost saving, one can conserve energy which might otherwise be required for the production of the more expensive gas mixture and the liquified gas.

The use of pressure swing adsorption techniques for the enrichment or recovering of gases from gas mixtures is state of the art. Generally speaking the pressure swing adsorption system is utilized to produce product gases of high purity and hence multistep or cascaded systems are utilized. Even with multistep processes the yield or recovery generally amounts to about 90%, i.e. about 10% of the component which is enriched, ultimately is found in a waste gas which is discharged.

With the system of the invention, utilizing the parameters and steps prescribed, the recovery or yield in terms of methane can be 99% or more, i.e. at most only 1% of the methane found in the mine gas is lost.

This is a significant advantage that valuable methane is not wasted or discharged. Of perhaps even greater importance is the fact that special procedures for removing the methane from the waste gases are unnecessary and that any methane which is discharged in the waste gas is at a concentration well below the explosive limit. The flaring off of methane containing waste gases and the disadvantages thereof are completely eliminated.

The present invention utilizes a single stage adsorption process in the sense that adsorption does not require a cascade of adsorbers, etc. The adsorption, uniflow expansion and counter-flow expansion and flushing can thus be carried out in a minimum number of adsorbers and practical results have shown that a product gas containing 50 volume percent methane can be economically obtained from a gas mixture (mine gas) containing 30% by volume methane with a methane yield of better than 99%.

Methane is a gas which is more strongly adsorbed than the other gases which are found in large concentrations in mine gas, namely nitrogen and air (oxygen). For the enrichment of gases which are more strongly adsorbed, it is common to desorb the gas by pressure reduction in the adsorbent. In the present case, however, the desorption is effected not only be expanding the gas to substantially standard pressure, but also by flushing the gas with the low-methane waste gas produced by adsorption of methane therefrom. While one might think that this would introduce a negative effect, in practice this flushing in conjunction with the other steps recited, results on the average in a gas mixture containing about 50 volume percent methane and also regenerates the absorbent for the next adsorption step with practically no methane breakthroughs in the waste gas from the subsequent adsorption stage.

Apart from the waste gas portions which are reused in the process, the waste gas which is discharged has only traces of methane.

The mine gases drawn off from the subterranean structures, depending upon the locations from which they are withdrawn and the time of withdrawal, tend to have methane concentrations which may fluctuate widely between about 25 and about 45% by volume. Since the product gas is to have a substantially constant concentration in methane, the degree of enrichment must be varied accordingly.

This can be achieved in accordance with the invention by raising the end pressure of the expansion-desorption step when the methane content in the mine gas increases or, alternatively, with a constant desorption/flushing pressure, lowering the adsorption pressure in response to the increase in the methane content of the mine gas. Either approach has the advantage that the timing or cadence of switchover of the pressure-swing steps need not be varied and that control can be effected by the comparatively simple expedient of regulating the pressure. It should be noted that such pressure regulation can be effected extremely rapidly in response to changes in concentration.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
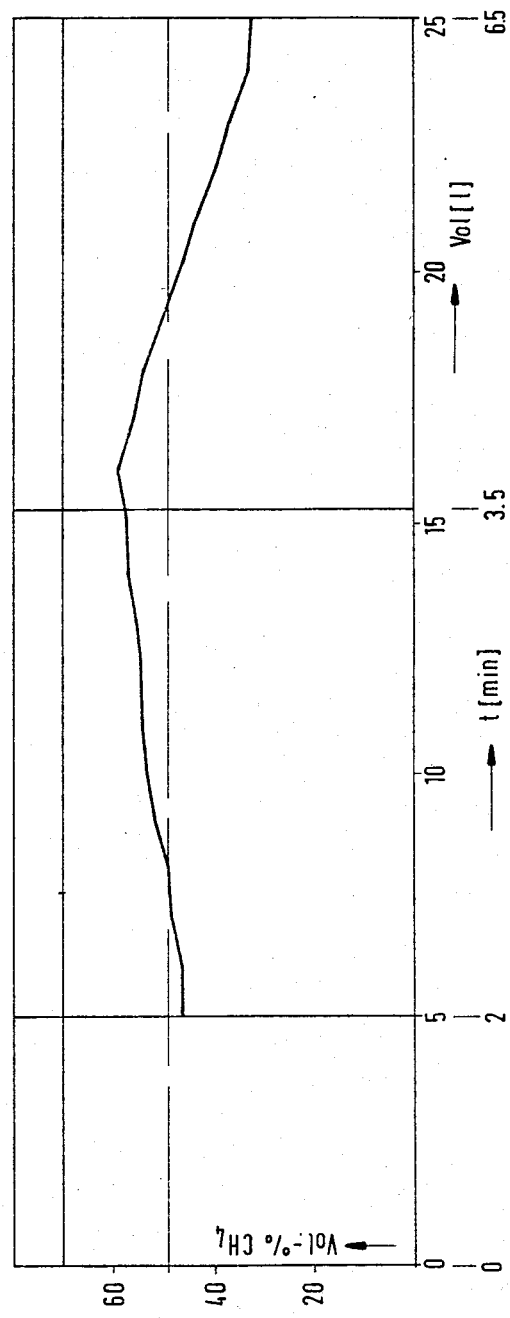
FIG. 1 is a graph in which volume percent of methane is plotted along the ordinate against time along the abscissa illustrating an example of the instant invention.

FIG. 1 shows the results for an individual test with a single adsorber operated in a pressure swing sequence and utilizing a carbon molecular sieve in the form of active carbon with a specific surface area of 820 m$^2$/g BET, an adsorber volume of 1.35 l, a crude gas containing 38.5 volume percent methane and 61.5 volume percent nitrogen and producing a product gas containing about 51 volume percent methane.

The adsorption pressure was about 5 bar.

During the adsorption phase, i.e. the phase in which the crude gas was introduced into the adsorbent at the adsorption pressure, the waste gas flowing from the adsorber was freed from methane to the extent that only traces remained therein. During uniflow expansion of the adsorber to 3 bar, the waste gases which were discharged also had at most traces of methane. The uniflow expansion was effected for 2 minutes and 5 l of the waste gas was obtained.

During the subsequent counterflow expansion, during an initial stage (first production stage), a gas mixture was withdrawn from the adsorber with a methane concentration which progressively increased from about 47 volume percent to about 58 volume percent, corresponding to a mean methane concentration during this production stage of 53 volume percent. At the conclusion of this counterflow expansion, the pressure in the adsorber was 1 bar and the counterflow expansion step was effected over a period of 1.5 minutes to yield 10.3 l of product gas.

In a second production step, methane-containing gas remaining in the adsorber was flushed therefrom at the adsorber pressure of 1 bar with a portion of the waste gas containing only traces of methane previously obtained. Surprisingly, unlike pressure-swing adsorption systems in which the concentration of the desired ingredient in the flushing gas drops sharply from the commencement of flushing, the concentration during flushing of methane in the flushing gas remains more or less constant before it falls materially.

As will be apparent from FIG. 1, indeed, there is a brief increase in the methane concentration in the flushing gas before a drop commences and there is a comparatively long duration in which the flushing gas contains product level quantities of methane.

Naturally, the flushing is interrupted before the concentration drops to a point, i.e. a threshold or set point value of methane concentration which will cause the mean or average methane concentration for the two production stages to fall below the desired level, in this case about 51% by volume methane. This cutoff can be 30% by volume or at a level thereabove as illustrated in FIG. 1. The cutoff of the flushing operation should be such that the average methane content during the flushing operation is 49% by volume so that when the production stage gases are combined, the methane content will be 51%.

The flushing stage can last about 3 minutes and yield 9.7 l of production gas.

Since the flushing operation takes place with methane concentrations which are comparatively high and the flushing is interrupted while a significant quantity of methane may remain in the adsorber, there is no danger that the product gas concentration will drop to a point which will detrimentally affect the overall quality of the product.

Once the flushing operation is terminated, the pressure in the adsorber is built up with a further portion of the waste gas containing only traces of methane obtained elsewhere and the cycle is repeated. Naturally a plurality of such adsorbers is generally used with waste gas from one adsorber being fed to other adsorbers for pressure buildup and flushing operations, thereby eliminating the need to store waste gas. The various adsorbers are functionally interchanged in an appropriate cadence.

Figure 2:
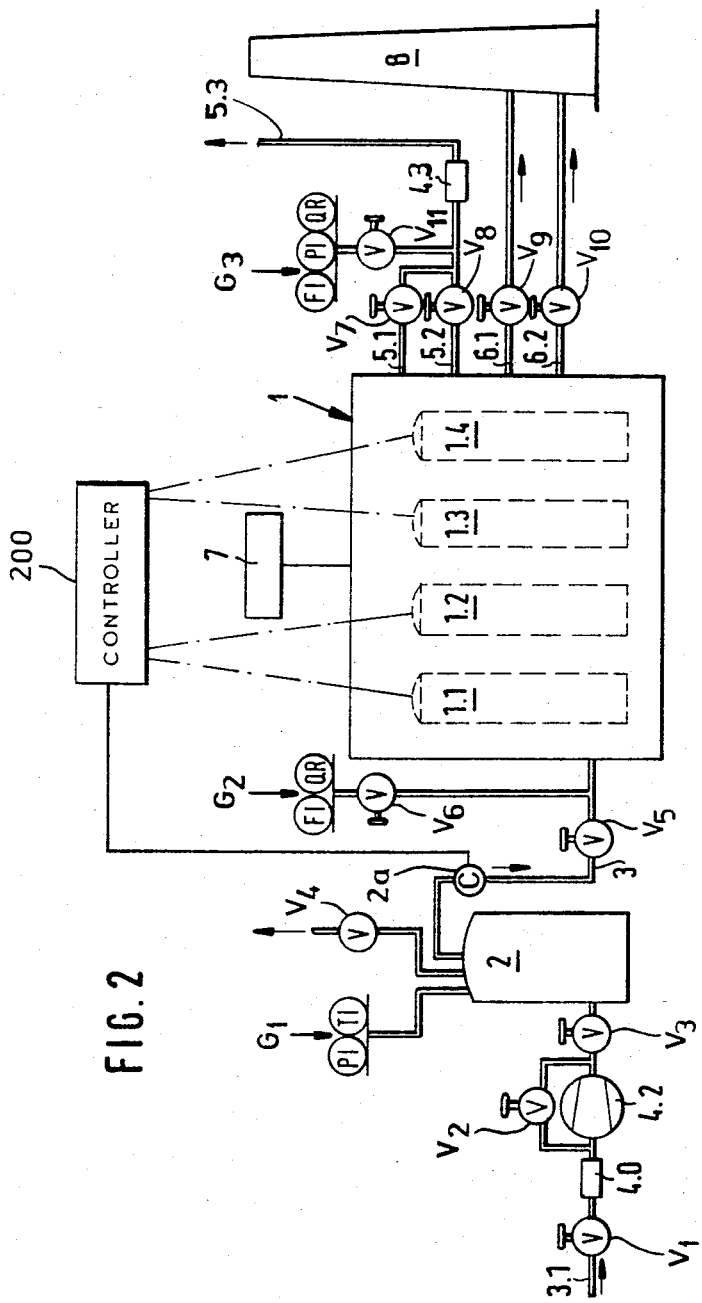
FIG. 2 is a flow diagram illustrating the application of the method of a multiadsorber system according to the invention.
Figure 3:
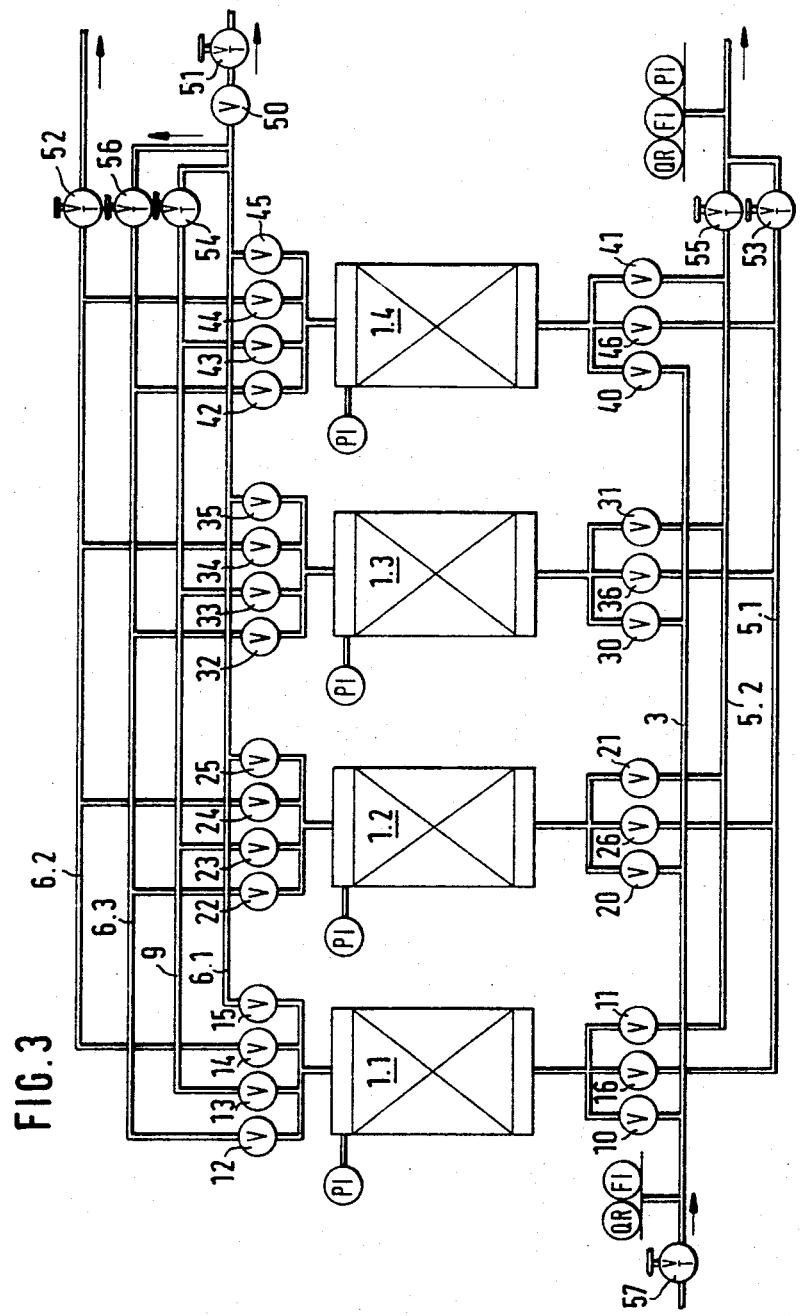
FIG. 3 shows a four-adsorber system.
Figure 4:
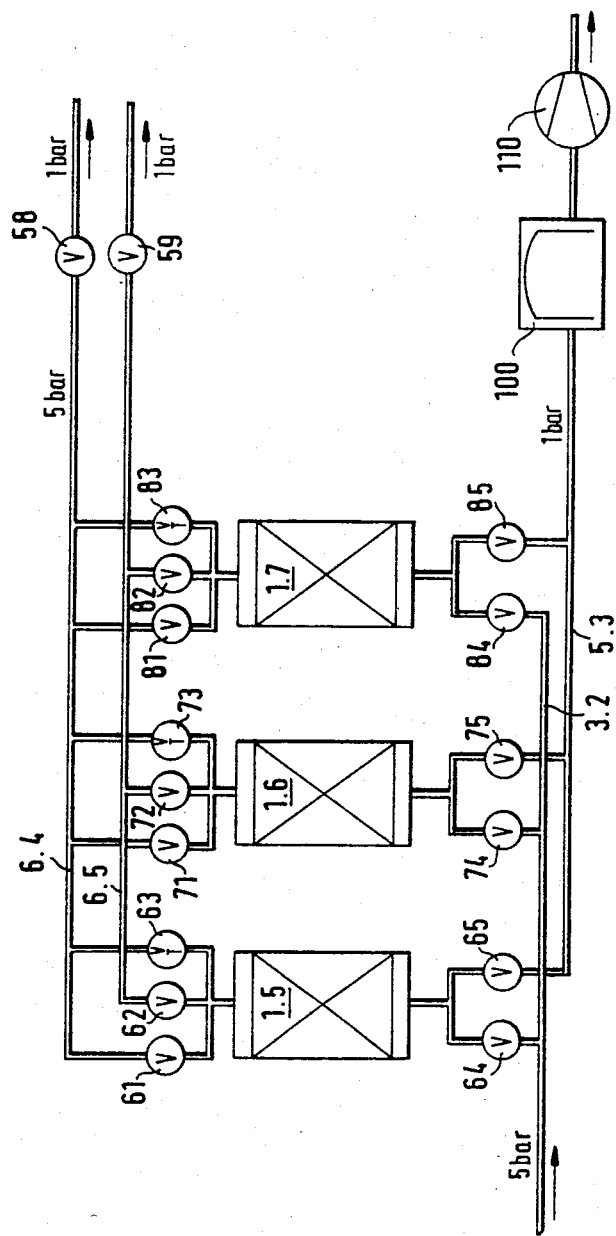
FIG. 4 is a flow diagram for a three-adsorber system for carrying out the invention.

Other examples of the invention are represented in the accompanying table and refer to the results obtained with the pressure-swing adsorber plate illustrated in FIGS. 2-4.

Example 1 represents a base example using the adsorber apparatus in FIG. 2 and which enriches the methane concentration of the crude gas, in this case mine gas, obtained as described from a methane content of 27.3% by volume to 49.8 volume percent. Example 2 also utilizes the four-adsorber system operating with a mine gas containing 38.5 volume percent methane. Examples 3 and 4 are examples utilizing a three-adsorber system (FIG. 3) for the enrichment of methane from a concentration of 38.5 volume percent, i.e. the same starting gas as in example 2, and a starting gas with a methane concentration of 29.8 volume percent, i.e. a starting gas with a methane concentration close to that of example 1, respectively to a product gas concentration of 49 volume percent.

Examples 5-7 depict the results obtained from the enrichment in methane concentration of low-methane mine gases utilizing four-adsorber pressure-swing systems with variation in the operating parameters to yield higher methane concentrations. Example 5 processes only a part of the gas by the pressure-swing apparatus for enrichment to 55.2 volume percent methane. Note that this value is not given in the table. This processed gas is then mixed with mine gas containing methane at 42.8 volume percent which bypasses the pressure-swing adsorber system to yield the desired product gas at 49.5 volume percent methane.

Example 6 shows the results obtained with a lower adsorber or charging pressure (6.5 bar by comparison with the 8 bar utilized in example 1-5 and 7). Example 7 shows the results obtained with a higher flushing pressure (2 bar as composed with the 1.1 bar of the other tabulated examples). Example 8 illustrates that by increasing the charging or adsorber pressure (to 12 bar as contrasted with the 8 bar of examples 1-5 and 7), higher methane contents in the product gas can be achieved (i.e. 58.5 volume percent).

FIG. 2 is a flow diagram illustrating an adsorber installation for carrying out the method of the invention, i.e. the methane enrichment of a mine gas. The adsorbers are here represented in broken lines at 1.1, 1.2, 1.3 and 1.4, respectively and are provided with the appropriate inlet and outlet valves for switchover and cycling as in pressure-swing adsorber systems generally, these valves allowing both uniform expansion and counterflow expansion and, of course, counterflow flushing all under the control of a sequence or timing system represented at 7.

Upstream of the adsorbers 1.1-1.4 a pressure supply is provided in the form of a tank 2 which can be maintained at an elevated pressure sufficient for adsorption in accordance with this invention, i.e. at least 5 bar and up to whatever pressure may be necessary to insure adsorber operation at 5 to 8 bar during the adsorption phase.

A crude gas inlet 3.1 can be connected to collection vessels, pipelines or suction pumps from the field of bore holes from which the mine gas is withdrawn, the mine gas passing via a valve $V_1$ through a flame arrester 4.0 and a compresser 4.2 which can have a bypass valve $V_2$ for controlling the pressure at the pressure side of the compresser. The compressed gas is admitted via a valve $V_3$ into the vessel 2.

The vessel 2 can be provided, in turn, with a venting valve $V_4$ which may be used for purging air from this vessel and with gauges $G_1$ providing pressure and temperature values as may be desired.

The feed line 3 communicating between tank 2 and the adsorbers 1.1–1.4 is provided with a further valve $V_5$, and a valve $V_6$ which allows gauges $G_2$ to be connected to the adsorbers to monitor conditions therein.

Within the adsorber unit 1 containing the adsorbers 1.1–1.4, the individual adsorbers may be switched over utilizing valves as illustrated in FIG. 3 and as will be described in greater detail hereinafter.

From the adsorbers 1.1–1.4, product lines 5.1 and 5.2 extend, these product lines being formed with valves $V_7$ and $V_8$, respectively, the product gases being delivered via a further flame arrester 4.3 to the product line 5.3.

In addition, waste gas lines 6.1 and 6.2 carry waste gases practically free from methane from the adsorber via valves $V_9$ and $V_{10}$ to a stack 8 which can discharge the gases into the atmosphere or permit further treatment thereof.

A set of gauges $G_3$ can be connected to the product line via valve $V_{11}$ to monitor the product gas. Throughout this disclosure, gauges PI can be considered to be pressure gauges, TI to be temperature gauges, FI to be flow rate monitors, QR to be composition detectors . . . . Naturally any other monitoring devices may be used as required.

Each of the adsorbers 1.1, 1.2, 1.3 and 1.4 is operated in the three sequential stages charging (adsorption), uniflow expansion, counterflow expansion and flushing, and pressure build up, the stages being offset in time so that a high pressure level in one adsorber can be communicated to another adsorber for pressure buildup, a low pressure level in an adsorber can be communicated to another adsorber for expansion or pressure reduction, etc.

By way of example, the adsorber 1.1 can be assumed to be at a pressure of about 8 bar (adsorption pressure) and in a phase in which it has been subjected to pressure buildup, i.e. contains methane free waste gas. During the adsorption phase it is supplied with mine gas from which the methane is adsorbed on the carbon molecular sieve of the adsorber 1.1. The waste gas leaving the adsorber 1.1 and containing only traces of methane is used to flush another one of the adsorbers or for pressure buildup therein.

After the termination of the adsorption phase for the adsorber 1.1, the mine gas is switched to the adsorber 1.2 while the adsorber 1.1 is expanded initially in uniflow and then in counterflow to the adsorption direction. During the uniflow expansion, the methane-free waste gas is discharged through the waste gas line 6.2 until the adsorber 1.1 drops in pressure to about 4 bar, substantially midway between the adsorption pressure of 8 bar and the flushing pressure of about 1.1 bar. During the following counterflow expansion, the methane rich product gas is discharged via the product gas line 5.1. When the counterflow expansion drops the pressure in the adsorber 1.1 to the flushing pressure of 1.1 bar, the flushing of this adsorber is commenced. During this phase, waste gas is passed through the adsorber 1.1 at the flushing pressure and methane-rich product gas is discharged. Consequently, during both the counterflow expansion and the flushing, product gas is obtained. The methane concentration of the product gas mixture has the desired product gas quality (concentration of methane) on average. In the last phase of the cycle, the absorber 1.1 is prepared for the next adsorption phase by raising the pressure in the adsorber from the flushing pressure of 1.1 bar to the adsorption pressure of 8 bar by admitting waste gas to the adsorber. A new adsorption cycle can then commence. The waste gas for flushing and pressure buildup thus can be withdrawn from one of the other adsorbers 1.2, 1.3, 1.4 in a respective phase of the cycling thereof and with appropriate staggering of the phases the other adsorbers pass through the same cycle each commencing with adsorption at the adsorption pressure of 8 bar.

Additional details of the apparatus will be apparent from the four-adsorber system shown in FIG. 3 which also utilizes adsorbers 1.1–1.4, one of which is to be considered as operating in the adsorption phase while the second adsorber is undergoing pressure buildup, a third adsorber is undergoing flushing and the fourth adsorber is in its uniflow and counterflow expansion phases.

The mine gas from line 3 can be admitted to the adsorber during the adsorption phase via a respective crude gas valve 10, 20, 30 or 40.

The waste gas produced during the adsorption phase is discharged via line 6.1 selectively under the control of one of the valves 15, 25, 35, and 45 and via a throttle valve 51 and a blocking valve 50 which, of course, is opened when gas discharged through the throttle valve 51 is desired.

At the conclusion of each adsorption step, in uniflow with the adsorption operation, the initial expansion phase is effected to reduce the pressure to a lower pressure substantially midway between the adsorption pressure and the flushing pressure with release of a waste gas which can be carried off via the waste gas line 6.2 and a selected waste gas valve 14, 24, 34, and 44 and via a throttle valve 52.

For the second counterflow expansion stage, which discharges a product gas into the product gas line 5.1, one of the product gas valves 16, 26, 36 or 46 is opened, the product gas being discharged via a throttle valve 53.

The second production phase is the flushing operation in which a flushing gas (waste gas) via a throttle valve 54 and a flushing gas line, is admitted through one of the flushing gas valves 13, 23, 33 and 43 to the end of the adsorber 1.1, 1.2, 1.3 or 1.4 opposite that to which the mine gas was supplied. The product gas stream during flushing traverses selectively one of the product gas valves 11, 21, 31 and 41 to the product gas line 5.2.

After flushing, the low pressure adsorber which has previously been flushed is brought back to the operating pressure (adsorption pressure) by waste gas via the throttle valve 56 from the waste gas line 6.1 and a pressure buildup line 6.3 selectively via one of the pressure buildup valves 12, 22, 32, and 42 for the commencement of a new cycle.

In FIG. 4 which shown a three-adsorber system, the adsorbers 1.5, 1.6 and 1.7 are similarly cycled through the phases as previously described. However, in this installation, while one of the adsorbers is in a pressure buildup stage prior to adsorption, a second is in its adsorption or charging phase while the third adsorber undergoes uniflow expansion, counterflow expansion and flushing during the same time interval.

The crude gas, e.g. mine gas, is fed via line 3.2 to the respective crude gas valve 64, 74 or 84 into the adsorber which is undergoing the charging or adsorption operation. The trace-methane waste gas is discharged by the respective waste gas valve 61, 71 or 81 to the waste gas line 6.4 and a throttle valve 58.

Upon termination of the adsorption stage, the initial uniflow expansion is effected from the adsorption pressure to an intermediate lower pressure with discharge of methane-free waste gas selectively via the respective waste gas valve 62, 72 or 82 and the waste gas line 6.5 and throttle valve 59.

The further counterflow expansion produces the first batch of product gas through the respective product gas valve 65, 75, 85 to the product gas line 5.3 to a gasometer, i.e. a device 100 capable of storing and equalizing the flow rate of the product gas. Finally the counterflow flushing phase is effected by admitting waste gas from line 6.4 through the respective valve 63, 73 or 83 which may also have a throttling function to enable the flushing operation to take place at the low flushing pressure. The flushing operation, as described, produces the second batch of product gas which is discharged into the line 5.3 via the product gas valve 65, 75 or 85. Generally the product gas is desired under a greater pressure than the low pressure of the adsorber during the expansion phases and for this purpose a compressor 110 can be provided downstream of the gasometer.

Each of the systems of FIGS. 3 and 4 can be provided with a controller, e.g. a microprocessor or microcomputer 200 which measures the methane content at 2A of the crude gas and regulates the adsorption pressure or flushing pressure. In particular, as the methane concentration in the crude gas increases, the adsorption pressure can be reduced or the desorption pressure increased in the manner previously described.

We claim:

1. A method of producing a product gas having a final methane content of about 50 volume percent which remains substantially constant from a crude gas having a variable but lower methane content by pressure-swing adsorption in at least one adsorber, said method comprising the steps of:

(a) adsorbing methane from said crude gas at an adsorption pressure between substantially 5 and 8 bar on a carbon molecular sieve adsorbent traversed by said crude gas in one direction to produce a waste gas containing only trace amounts of methane;

(b) thereafter expanding said adsorbent to an expansion pressure substantially between 2.5 and 5 bar and substantially midway between the adsorption pressure and a subsequent flushing pressure while discharging a waste gas containing only trace amounts of methane in uniflow to the adsorption;

(c) thereafter expanding the adsorbent to the flushing pressure between substantially 1.1 and 2 bar in counterflow to the adsorption and recovering a first portion of product gas containing about 50 volume percent methane therefrom in a first product stage; and (d) flushing said adsorbent in counterflow to the adsorption with a waste gas containing only trace amounts of methane from steps (a) or (b) at said flushing pressure to produce a second portion of product gas containing about 50 volume percent methane therefrom, combining said portions of said product gas forming said product gas having said final substantially constant methane content of about 50 volume percent.

2. The method defined in claim 1, further comprising the step of controlling the flushing pressure to increase the magnitude thereof with increasing methane concentration in said crude gas.

3. The method defined in claim 1, further comprising the step of reducing the adsorption pressure in step (a) with increasing methane concentration of said crude gas.

4. The method defined in claim 1 wherein said crude gas is a mine gas obtained from bore holes around mine galleries, tunnels and shafts and having a methane content of 25 to 45 volume percent.

5. The method defined in claim 2 wherein said crude gas is a mine gas obtained from bore holes around mine galleries, tunnels and shafts and having a methane content of 25 to 45 volume percent.

6. The method defined in claim 3 wherein said crude gas is a mine gas obtained from bore holes around mine galleries, tunnels and shafts and having a methane content of 25 to 45 volume percent.

TABLE

| | | Example | | | | | | | |
|---|---|---|---|---|---|---|---|---|---|
| | | 1 | 2 | 3 | 4 | 5 | 6 | 7 | 8 |
| | Technological Parameter | | | | | | | | |
| 1 | Number of Adsorbers | 4 | 4 | 3 | 3 | 4 | 4 | 4 | 4 |
| 2 | Cycle Time for 1 Complete Cycle (min.) | 40 | 20 | 36 | 60 | 32 | 32 | 32 | 32 |
| 3 | Capacity per Adsorber (m$^3$) | 10 | 7 | 10 | 14 | 10 | 10 | 10 | 10 |
| 4 | Methane Conc. of Mine Gas (Vol.-%) | 27.3 | 38.5 | 38.5 | 29.8 | 42.8 | 42.8 | 42.8 | 36.5 |
| 5 | Charging (Adsorption) Pressure (bar) | 8.0 | 8.0 | 8.0 | 8.0 | 8.0 | 6.5 | 8.0 | 12 |
| 6 | Expansion Pressure (bar) | 2.7 | 3.0 | 3.0 | 2.8 | 3.2 | 3.1 | 5.1 | 2.8 |
| 7 | Flushing Pressure (bar) | 1.1 | 1.1 | 1.1 | 1.1 | 1.1 | 1.1 | 2.0 | 1.1 |
| 8 | Crude Gas Flow Rate (m$^3$/h) | 4,040 | 2,830 | 3,000 | 3,825 | 5,769 | 2,505 | 3,042 | 3,868 |
| | Methane Flow: | | | | | | | | |
| 9 | Bypass (m$^3$/h)* | — | — | — | — | 1,334 | — | — | — |
| 10 | Adsorber (m$^3$/h)* | 1,103 | 1,090 | 1,155 | 1,140 | 1,135 | 1,072 | 1,302 | 1,412 |
| 11 | Waste gas (m$^3$/h)* | <1 | <1 | <1 | <1 | <1 | <1 | <1 | <1 |
| 12 | Counterflow Expansion (m$^3$/h)* (Product Gas 1) | 398 | 467 | 363 | 370 | 385 | 362 | 324 | 641 |
| 13 | Flushing (Product Gas 2) (m$^3$/h)* | 705 | 623 | 792 | 770 | 750 | 710 | 978 | 771 |
| 14 | Product Gas Total (m$^3$h)* | 2,216 | 2,200 | 2,333 | 2,303 | 5,173 | 2,166 | 2,630 | 2,430 |
| 15 | Methane Content (Vol.-%) | 49.8 | 49.5 | 49.5 | 50.5 | 49.5 | 49.5 | 49.5 | 58.1 |
| 16 | Methane Yield (%) | >99.9 | >99.9 | >99.9 | >99.9 | >99.9 | >99.9 | >99.5 | >99.5 |

*All m$^3$/h values are given for a pressure of 1.013 bar and a temperature of 0° C.